(12) United States Patent
Siddiqui (10) Patent No.: US 6,876,721 B2
(45) Date of Patent: Apr. 5, 2005

(54) METHOD FOR DEPTH-MATCHING USING COMPUTERIZED TOMOGRAPHY

(75) Inventor: Shameem Siddiqui, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 194 days.

(21) Appl. No.: 10/349,292

(22) Filed: Jan. 22, 2003

(65) Prior Publication Data

US 2004/0141583 A1 Jul. 22, 2004

(51) Int. Cl.[7] ............................................. G01N 23/06
(52) U.S. Cl. ............................ 378/52; 378/53; 378/4; 250/269.3
(58) Field of Search ...................... 378/52, 53, 4–20; 73/152.07; 250/269.1, 269.3, 255

(56) References Cited

U.S. PATENT DOCUMENTS

| | | | |
|---|---|---|---|
| 4,312,040 A | 1/1982 | Tinch et al. | |
| 4,320,469 A | 3/1982 | Frawley et al. | |
| 4,346,593 A | 8/1982 | Howells et al. | |
| 4,355,357 A | 10/1982 | Chan | |
| 4,542,648 A | 9/1985 | Vinegar et al. | |
| 4,623,792 A | 11/1986 | Bohme et al. | |
| 4,755,944 A | * 7/1988 | Glass | 702/7 |
| 4,868,751 A | 9/1989 | Dogru et al. | |
| 5,036,193 A | 7/1991 | Davis, Jr. et al. | |
| 5,359,194 A | 10/1994 | Moss | |
| 5,360,066 A | * 11/1994 | Venditto et al. | 166/250.1 |
| 5,556,884 A | 9/1996 | Oberdorf | |
| 5,581,024 A | 12/1996 | Meyer, Jr. et al. | |
| 5,984,023 A | 11/1999 | Sharma et al. | |
| 6,003,620 A | 12/1999 | Sharma et al. | |
| 6,006,844 A | 12/1999 | Van Puymbroeck et al. | |
| 6,088,656 A | 7/2000 | Ramakrishman et al. | |
| 6,115,671 A | 9/2000 | Fordham et al. | |
| 6,220,371 B1 | 4/2001 | Sharma et al. | |

* cited by examiner

Primary Examiner—Craig E. Church
Assistant Examiner—Krystyna Suchecki
(74) Attorney, Agent, or Firm—Abelman, Frayne & Schwab (57) ABSTRACT

In order to correlate information of a core sample taken from a borehole with information derived from an original position of the core sample in the borehole, the core is scanned using computed tomography (CT) to generate core slices having first depths assignable thereto based upon a drilling record. The core slices are concerted to first bulk density data using either region-of-interest statistics or selective histogram statistics, which is then compared to second bulk density data obtained from logging at respective second depths to obtain a good match between the first and second depths.

15 Claims, 11 Drawing Sheets

METHOD FOR DEPTH-MATCHING USING COMPUTERIZED TOMOGRAPHY

FIELD OF THE INVENTION

This invention relates to oil/gas field drilling, and more particularly to an improved method for identifying the correct depths of reservoir core samples that are retrieved from a borehole.

BACKGROUND OF THE INVENTION

In drilling operations for oil and gas, the retrieval of cylindrical samples of rock materials, known as cores, from underground locations is a common practice. The cores are studied to gain a better understanding of the fabric of the reservoir materials and their inherent properties to store and flow oil, gas and water.

One common method of gaining information on the reservoir material properties is to take continuous measurements of the wellbore properties for each well using electrical, sonic, radioactive and other devices, a process known as logging. If the information in the log for a particular depth in the wellbore can be combined with the information derived from a core sample taken at that depth, a fuller understanding of the reservoir is possible. However, in order to extract meaningful data from the logs for this purpose, it is essential to be able to match the depth as recorded in the log with the core sample taken at that depth.

Unfortunately, this is not a straightforward process. In general, the depth at which a particular core is taken as recorded by the drilling crew is subject to large errors as the depths are calculated by adding the lengths of individual drill pipes, which are subject to various expansion-compression loads in the borehole. Additionally, the incomplete recovery of cores (i.e. some pieces are missing due to mechanical failure and drilling fluid circulation related wash-outs), coupled with the current practice of lumping all the unrecovered lengths at the bottom of each core barrel, which is a tube holding cores during drilling, also contributes to the uncertainty in core depth reporting. The errors or uncertainties can lead to improper matches between log and core data, resulting in costly mistakes in reservoir performance predictions.

One conventional method for attacking this problem has been gamma-scanning in petrophysical laboratories for comparing the core depths with log depths. While gamma-scanning is easy to apply in sandstone reservoirs, the absence of the usual markers present in the typical sand/shale sequences and poor signals make it difficult to obtain satisfactory depth matches in the carbonate cores.

In another aspect of oil/gas field drilling, X-ray computed tomography of cores has been used to measure, for example porosity, relative permeability, fluid saturations, bulk density and mineralogy. The process makes it possible to look inside core materials in a non-destructive manner for visualizing heterogeneities, lithology variations and has been used to compute such core parameters for almost 20 years. Examples of patents disclosing the use of this process are U.S. Pat. Nos. 5,036,193, 4,868,751, 5,359,194, 5,984,023, 6,003,620 and 6,220,371 B1.

U.S. Pat. No. 4,542,648 to Vinegar et al. is directed to the use of an X-ray computerized axial tomography (CAT) scanning technique in a method of correlating a core sample with its original position in a borehole. This method recognizes that there is a relationship between certain quantitative data (mass attenuation coefficients) generated by a typical CT scanner and bulk densities at generally high X-ray energies. In one embodiment, the method involves convolving interpolated density values derived from CT measured average attenuation coefficients with the response function of the logging tool to generate convolved density values that are cross correlated with the log density values to obtain the maximum cross correlation function for the correlation depth. In another embodiment, the method involves convolving effective atomic numbers with the response function of the tool to obtain convolved effective atomic numbers that are cross correlated with the photoelectric log values.

However, this method requires the use of complicated mathematics, which makes its procedure difficult for use by typical workers for predicting depth shifts. Moreover, with this method it is difficult to correlate the CT data with the density logs as it depends on what was present outside the core material.

SUMMARY OF THE INVENTION

It is therefore an object of the present invention to provide a method of matching log depths to core depths that avoids the above-described difficulties of the prior art.

It is a further object of the present invention to provide a method of depth shifting to provide improved results in matching log depths to core depths.

It is a more specific object of the present invention to provide a method of depth shifting using computed tomography (CT) to improved results in matching log depths to core depths.

The above and other objects are achieved by the present invention, which, in one embodiment, is directed to a method of depth shifting to correlate information of a core sample taken from a borehole with information derived from an original position of the core sample in the borehole. The method comprises the steps of defining a plurality of scan locations at selected intervals along the core, scanning the core at each scan location using computed tomography (CT) to generate a respective core slice for each scan location, each core slice including CT data at the respective scan location and each core slice further having a respective first depth assignable thereto based upon a drilling record taken during drilling of the borehole, generating region-of-interest statistics or selective histogram statistics for each core slice, converting the CT data for each core slice to first bulk density data in accordance with standardized CT number data and the respective region-of-interest statistics or selective histogram statistics, comparing the first bulk density data to the second bulk density data obtained from logging at respective second depths along the borehole, and determining depth shifting appropriate for obtaining a good match between the first and second depths.

In accordance with an advantageous aspect of the present invention, the region-of-interest statistics are circular region-of-interest statistics. In the event that all slices contain fractures or broken pieces, the region-of-interest can be a smaller sub-region of the circular region representing the slice, such as a smaller circle or a polygon.

In accordance with an advantageous aspect of the present invention, the selective histogram statistics refers to calculating mean CT numbers in the significant portion of the overall CT number histogram representing the rock material only, for a sample with non-rock material (air) presence (such as plug holes, plugging/slabbing related missing parts, or gap between two adjacent drilled cutting fragments). The significant portion of the overall CT number histogram is selected by isolating the CT number range representing the peak of high CT numbers of the bi-modal distribution of overall CT numbers in this case. The non material presence in this case is represented by the peak of low CT numbers.

In a preferred embodiment, the converting step includes steps of generating statistical CT number data for each core slice based upon the respective CT data and region-of-interest or selective histogram statistics, generating slice bulk density data for each core slice based upon the respective statistical CT number data and the standardized CT number data, and calculating at least one average bulk density over the core based upon the slice bulk density data.

These and other objects, features and advantages of the present invention will be apparent from the following detailed description of the preferred embodiments taken in conjunction with the following drawings, wherein like reference numerals do not like elements.

DETAILED DESCRIPTION OF THE PREFERRED EMBODIMENTS

Computed Tomography (CT), and in particular X-ray computed tomography, is a well known technique in many applications wherein a specimen is bombarded with X-rays and the resultant signals are processed to provide a corresponding image of the specimen indicating certain desired characteristics. Generally, a CT scanning system produces a display or image of a characteristic distribution in a cross-section or transverse slice of the specimen, e.g. a core. X-ray energy is passed through a sample slice and falls on a detector. After a desired number of scans are completed for each sample slice, the next sample slice is placed within the path of the X-rays. Signals from the detector are then processed and applied to a display or recording system. The above-mentioned U.S. Pat. No. 4,542,648 provides a discussion of CT, which is incorporated herein by reference. Because this technique is well known, it will not be further explained herein.

As indicated above, the present invention relates to the use of CT scanning for depth matching of cores to drilling log or "wireline" information. The CT scans on these cores from vertical wells produce high quality images of the entire cored section at a finer spacing than well logs. By using a technique involving qualitative screening of the various CT slices and their region-of-interest based statistics or selective histogram statistics, meaningful pseudo-bulk density logs can be generated. These logs can then be placed side-by-side with the bulk density logs in order to determine how the depths for one set of data should be shifted to match the depths of the other set of data in accordance with an established standard for good matching, i.e. the required depth shifts.

In accordance with the preferred embodiments, the present invention is directed to a method using the data produced by an X-ray CT-scanner on preserved or unpreserved core samples to generate the pseudo-bulk density logs which are then placed side-by-side with the bulk density logs generated by wireline methods in order to predict the depth shifting needed. the method generally involves the following steps (each of which may include a number of subsidiary steps).

1) Generate several calibration tables or (depending on scanners) for all possible sizes of the core to be scanned. Best results are obtained by using a solid phantom (a cylindrical object used for calibration) made of a homogeneous material with grain density close to the rock to be scanned (e.g. Macor for carbonates, Quartz for sandstones) with a diameter slightly larger than the tube containing the core for example. There should be several calibration tables (or disks, depending on the scanner) available for various combinations of X-ray voltage (preferably 120, 130 and 140 kV), X-ray amperes (e.g. 50, 100, 125, 200 mA), and X-ray beam thicknesses (2 mm, 5 mm, 10 mm, etc.).

2) Receive cores from the field or core storage (typically either preserved in brine inside PVC core tubes or fiberglass or aluminum sleeves, or unpreserved and in plastic or metal trays), advantageously in about 3 foot sections. Identify the need for support and centering on the positioning table for the core to be examined.

3) Place the sample on the scanning table (or "couch") and take scans with various energy-thickness combinations, by changing calibration tables or disks, to test which combination gives the best images, i.e. without the beam hardening artifact which is common in CT-scanning.

4) Select a possible analysis technique based on the condition of the sample—use an ROI statistics based technique for whole cores and plugs that are intact, with very few breakages, and use a selective histogram based technique for samples that are plugged and/or slabbed or for drilled cuttings in sample bags.

5) Align and push the core to one end of the core box by tilting (for a preserved core, on a machine without the pilot-scan option) or by pushing to one side of the sample tray (for an unpreserved core). Scan at a high X-ray energy, advantageously 120, 130 or 140 kV, at regular intervals advantageously 2 inches, starting at a fixed mark near the top depth of the core in the tube or tray, advantageously 3 inches from the top depth, which results in about 16 slices per core tube or tray. Each core "slice" is a 3-D reconstruction of the CT data at one scan location. Complete scanning of all the core tubes or trays at the same condition.

6) Scan various calibration "standards" (usually Quartz, Macor, Air, water and clean carbonate and clean sandstone samples of known densities) in the same condition as the core. The purpose is to generate bulk density vs. CT number relationships for the known "standards."

7) Transfer raw data to an image processing workstation with software capable of alignment, region-of-interest (ROI) statistics, histogram analysis, and beam hardening correction, as well as any conventional correction methods as required.

8) Align the core between the first and last slices with the software, draw circular ROI and store statistical data on the CT number mean, standard deviation, minimum, maximum, etc.

9) Do a quality-control check of each "slice" to find whether it contains fractures, breaks, or is otherwise incomplete within the ROI. Mark slices with such problems with a significance flag to omit them from future calculations.

10) For samples that qualify for selective histogram statistics (plugged and slabbed samples, drilled cuttings, etc.), use overall CT number distribution data on one of the representative core plugs to identify the significant CT number range representing the rocks. Then use that range and histogram analysis (typically 10 to 15 bins) to get mean CT numbers at each slice location for all the samples scanned.

11) Transfer statistical data files to a spreadsheet and assign depths to each "slice" based on driller's record.

12) Convert the mean CT number data to bulk density by comparing this data to the bulk density vs. CT number relationships seen in known "standards."

13) Take the average bulk density over each tube length (or take two averages if two distinct density trends exist within one tube or tray), and plot the bulk densities along with their log counterparts.

14) Determine and apply the appropriate depth shifting to the driller's depths until there is a good match between the two sets. For the purpose of actually shifting the data, it is possible to use either manual shifting or the conventional shift feature available in log analysis software such as GEOLOG.

15) Record and apply the depth-shifting scheme to all slice depths. Present data in the reports for future use.

Figure 1:
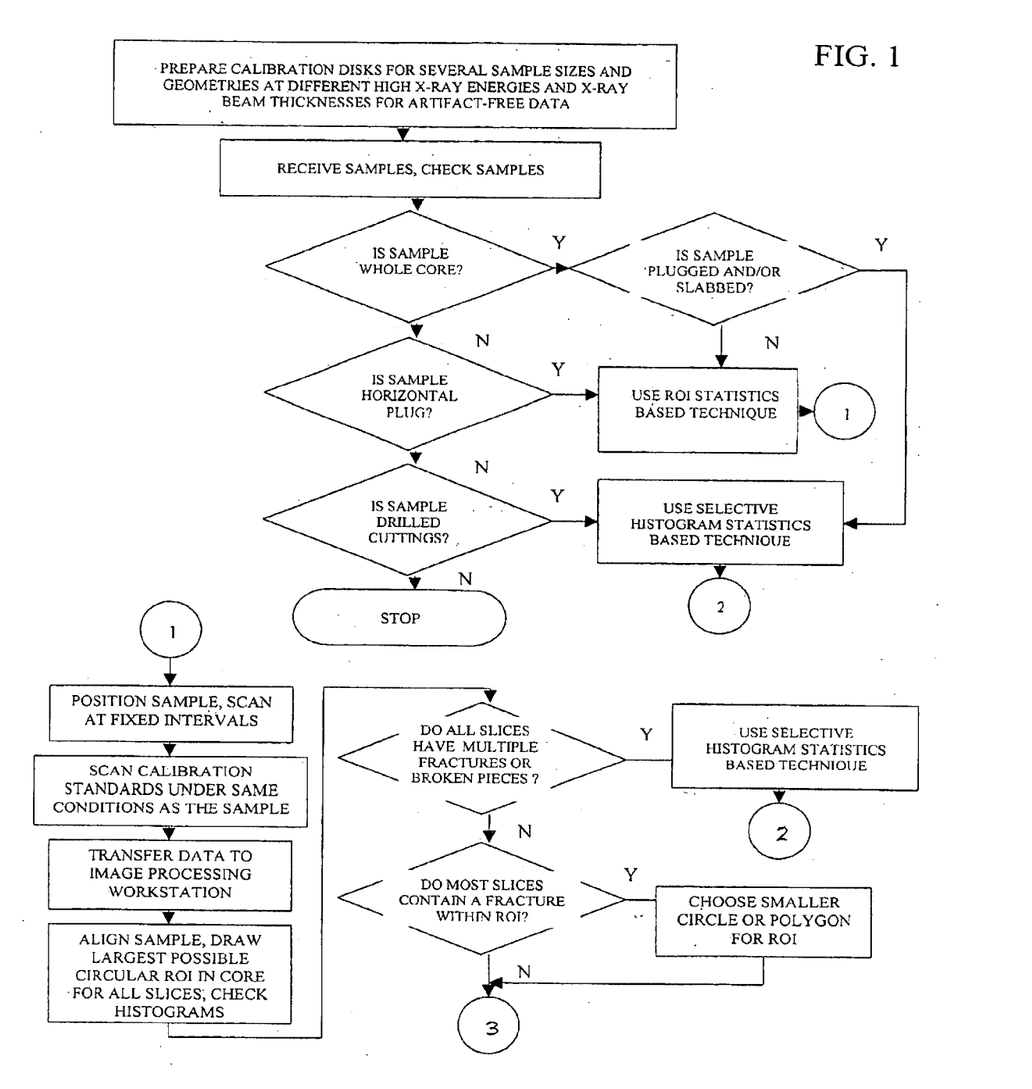
FIG. 1 is a flowchart of the method in accordance with a preferred embodiment of the present invention.
Figure 2:
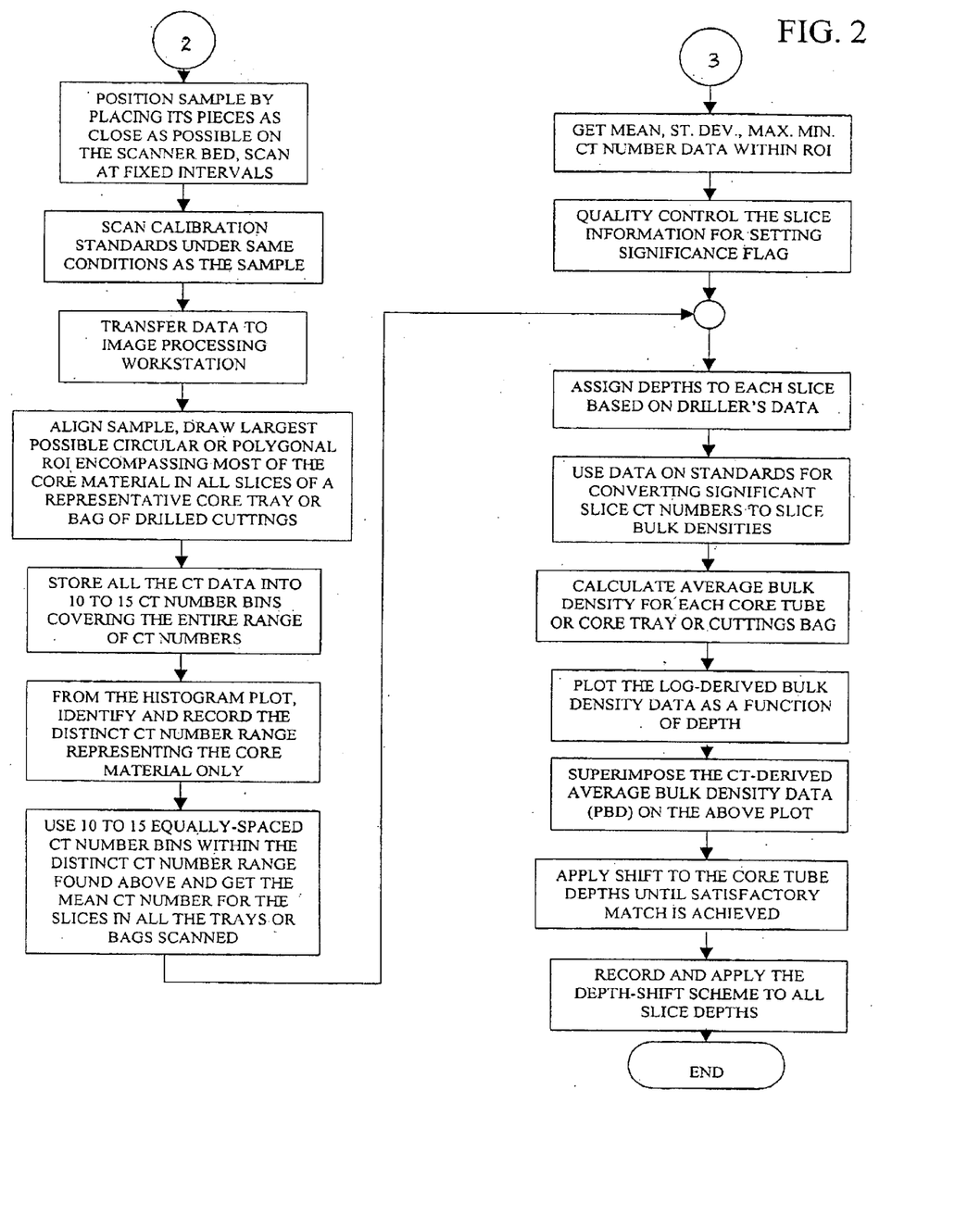
FIG. 2 is the continuation of the flowchart shown in FIG. 1.

FIG. 1 and FIG. 2 are the flowcharts of the inventive method. Sample results achieved by the inventive methods will now be discussed.

Figure 3:
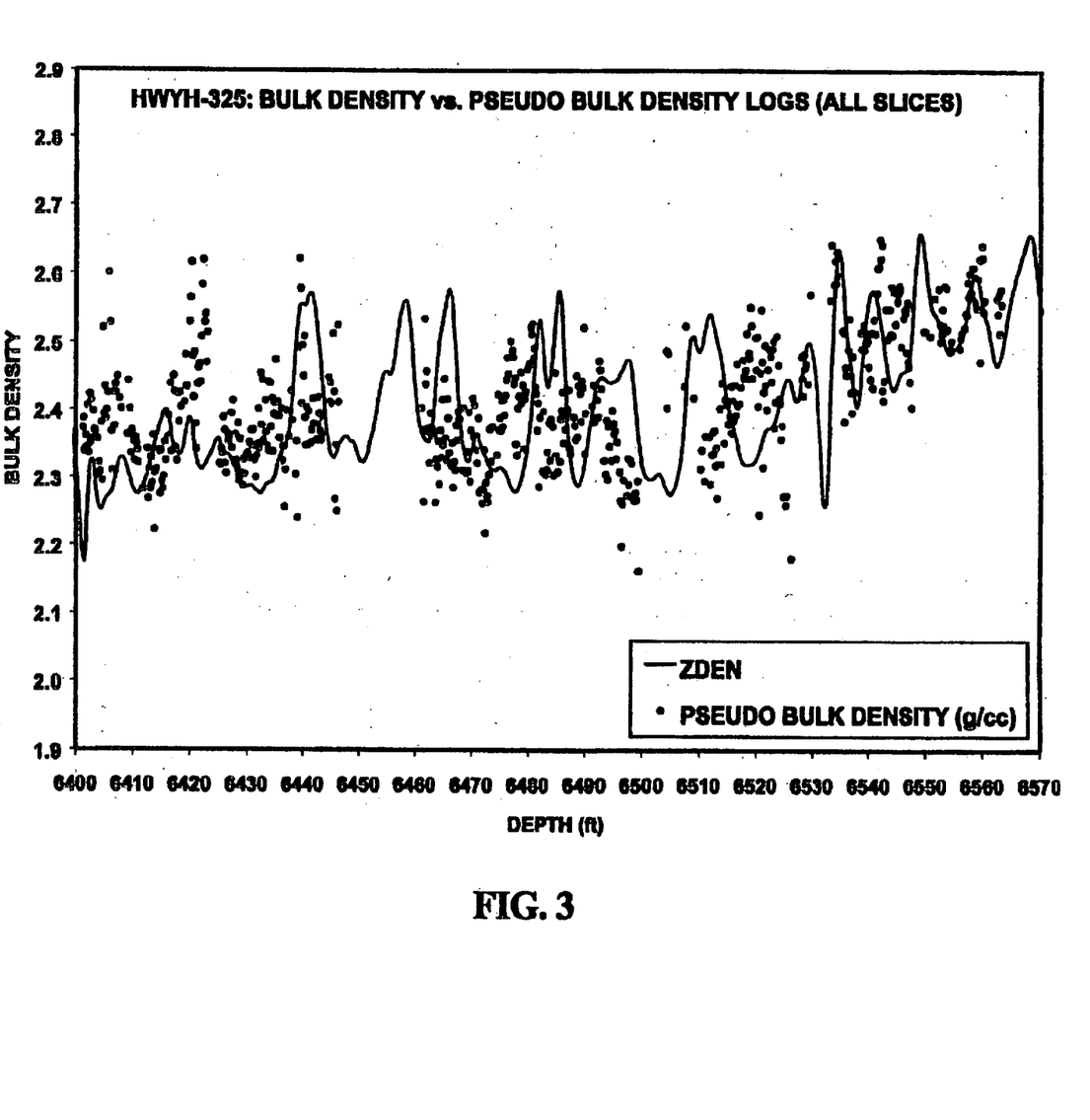
FIG. 3 is a plot of the pseudo-bulk density (PBD) values calculated from CT data plotted against the bulk density log (ZDEN) for a cored interval.

FIG. 3 illustrates the pseudo-bulk density (PBD) values calculated from the CT data plotted the bulk density log (ZDEN) for the cored interval. The results show a good overall match between the two sets of independent data.

For this figure, the bulk density logs are taken at 6 inch intervals and the data were smoothed, whereas the CT data were taken at 2 inch intervals and no smoothing was applied. The scatter seen in the CT-derived PBD values is common in objects for the scale used. The concentration of data points in FIG. 3 indicates that there may be some shifting required to match the log depths with the reported core depths (driller's depths).

Figure 4:
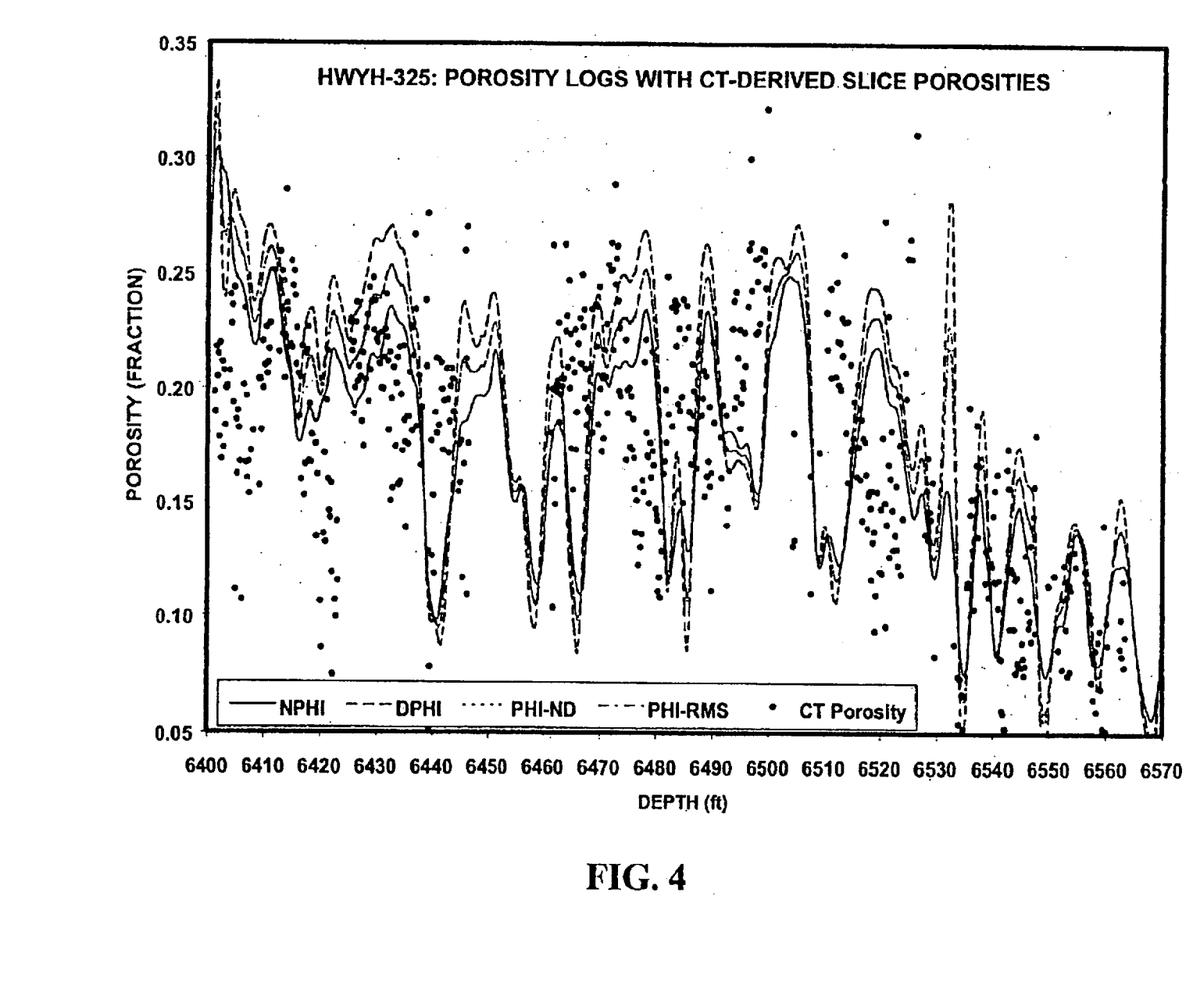
FIG. 4 illustrates a number of different porosity logs plotted against the CT-derived slice porosities.

FIG. 4 illustrates a number of different porosity logs plotted against the CT-derived slice porosities. The porosity logs include neutron porosity (NPHI), density porosity (DPHI), mean of neutron and density porosities (PHI-ND) and the root-mean-squared porosities (PHI-RMSD).

Figure 5:
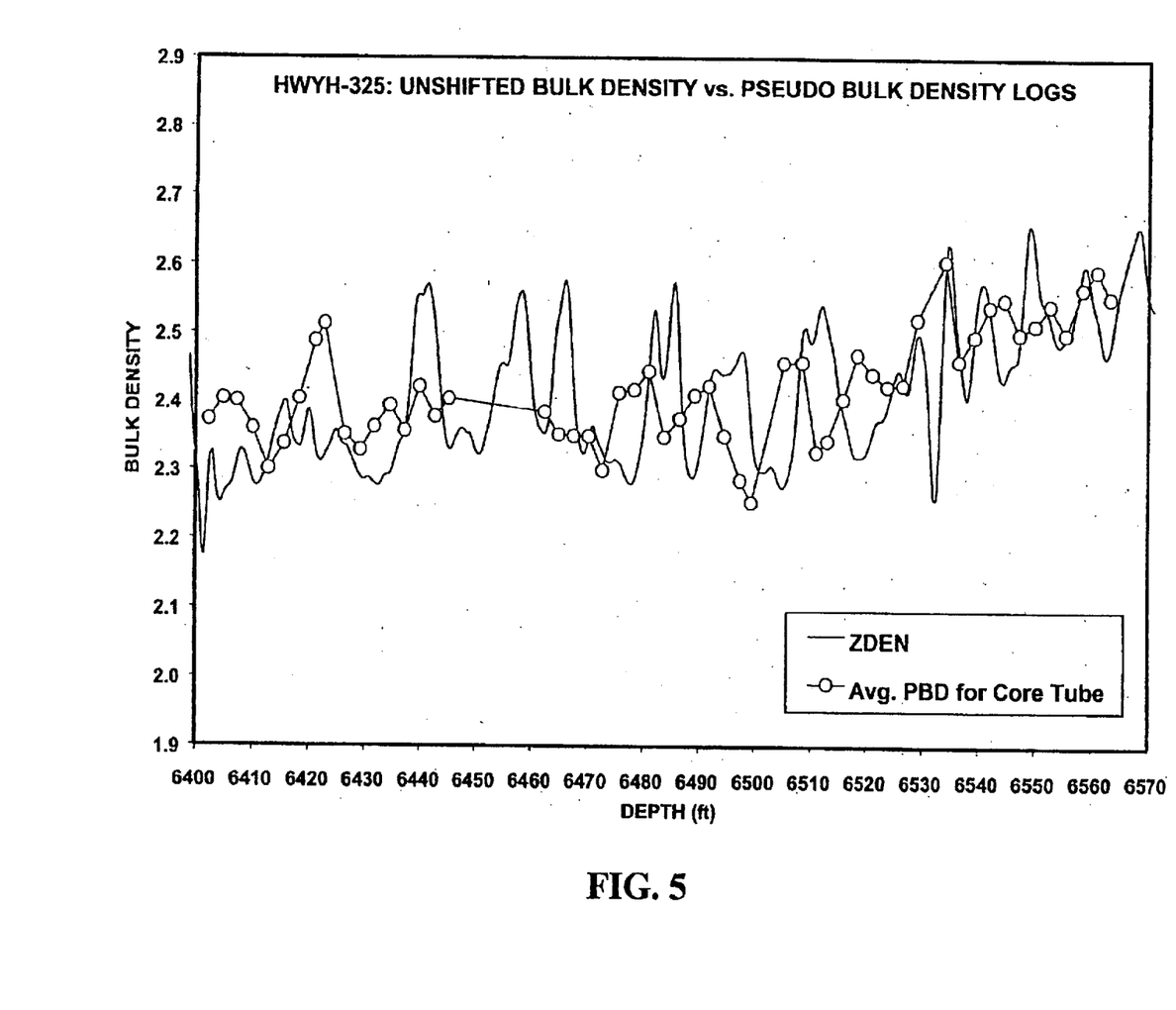
FIG. 5 is a plot of the average PBD values for each core tube plotted against the bulk density log data (ZDEN).

FIG. 5 is a plot of the average PBD values for each core tube plotted against the bulk density log data (ZDEN). As may be seen from FIG. 5, the scatter shown in FIG. 3 can be largely removed by taking the average PBD values with the average depth of the core tube. The figure also shows the need for shifting the depths in order to get a good match between the log-derived and CT-derived bulk density values.

In order to determine the appropriate depth shift, a depth-shifting scheme was used in which various shifts were tried to match the CT-derived bulk density data with the bulk density log data. The shift was applied to the CT-derived data only. The following figures illustrate the depth-shifting scheme and its results.

Figure 6:
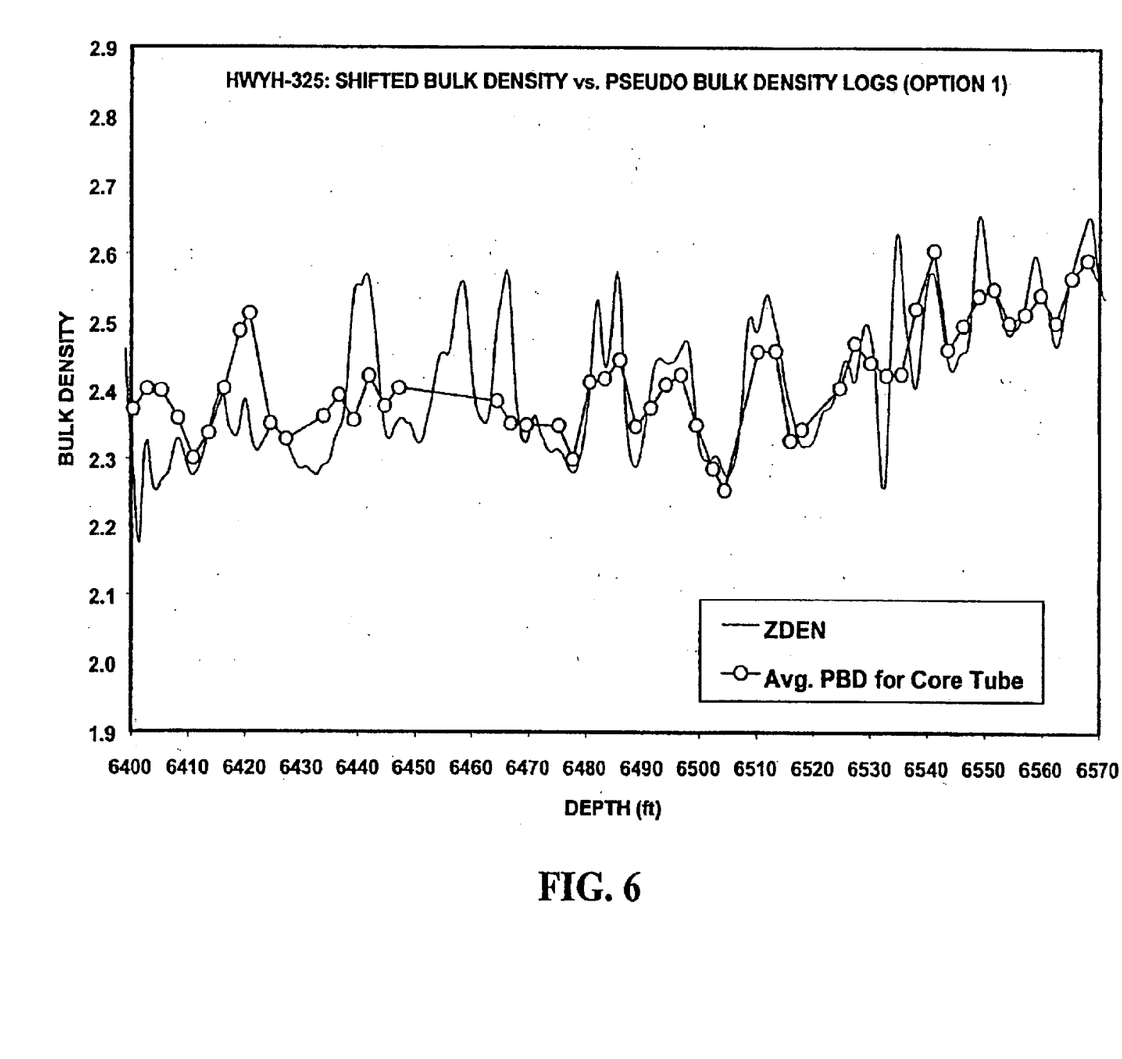
FIG. 6 illustrates the depth-shifted PBD data plotted against the ZDEN data.

FIG. 6 illustrates the depth-shifted PBD data plotted against the ZDEN data. The maximum shift in the well for this illustration was 20 ft, which is less than the total length of unrecovered cores from the cored interval, which was 24.4 feet.

Figure 7:
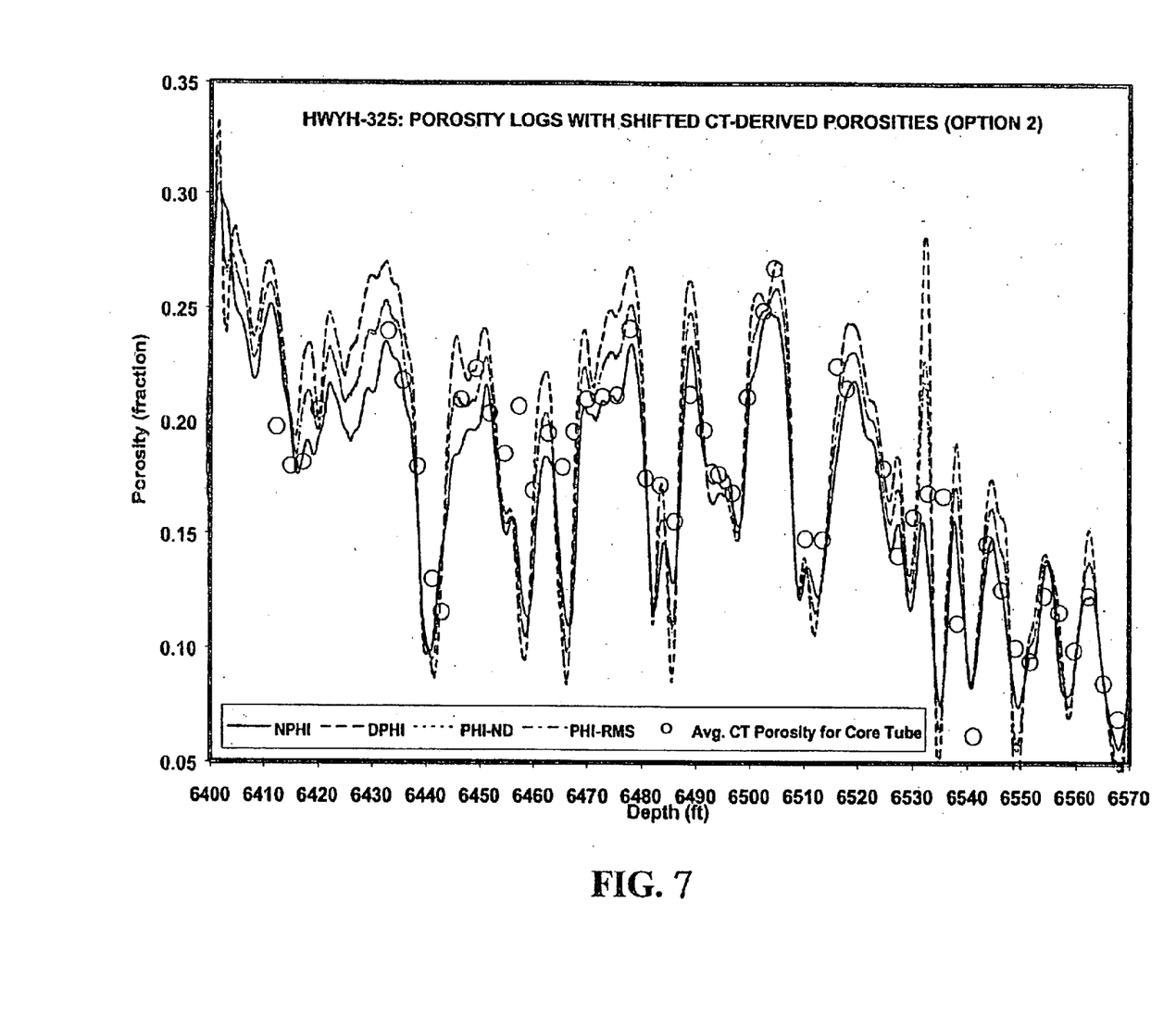
FIG. 7 shows the depth-shifted CT-derived porosities (using the second option) against the four porosity logs of FIG. 3.

FIG. 7 shows the depth-shifted CT-derived porosities plotted against the four porosity logs. The depth shifting applied appears to have made a much better match between porosities derived from CT and log sources.

Figure 8:
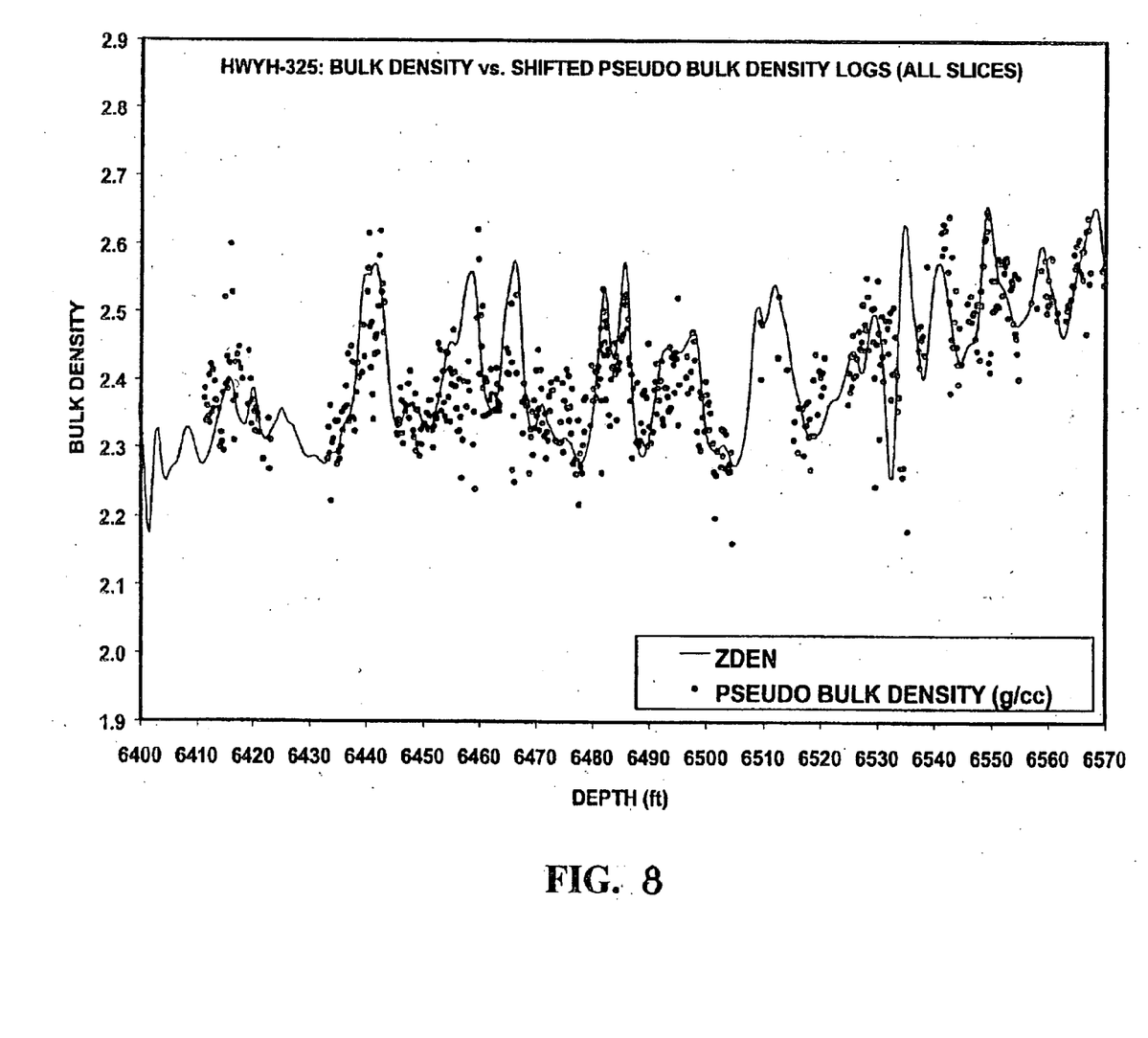
FIG. 8 illustrates slice-by-slice bulk density data, shifted using the second option and plotted against the bulk density log ZDEN.

FIG. 8, with slice-by-slice bulk density data shifted using the depth-shifting scheme and plotted against the bulk density log (ZDEN), also corroborates the conclusions of a better match.

Figure 9:
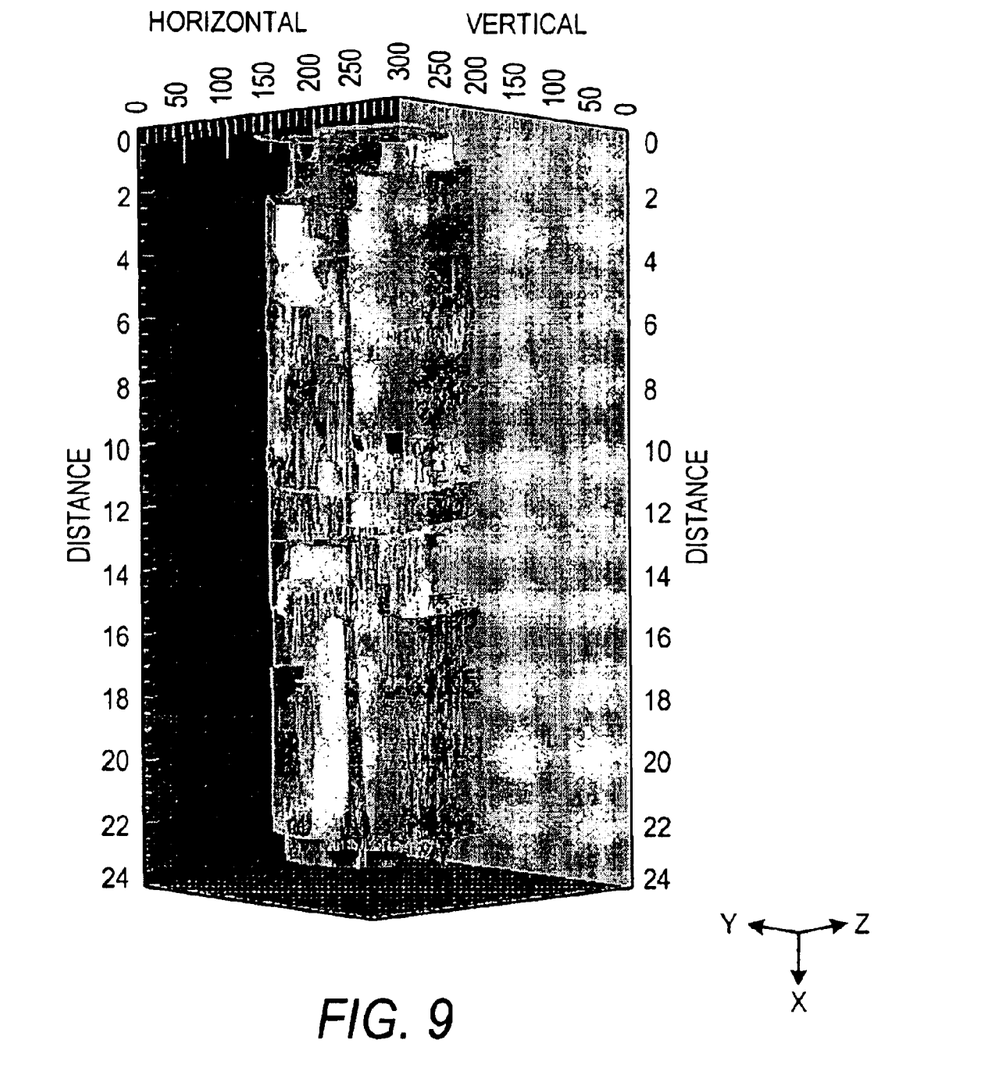
FIG. 9 illustrates a CT-generated three-dimensional representation of a 3-ft section of core that was plugged (drilled to extract smaller samples) and slabbed (sliced along the length for geological studies) prior to scanning and for which the selective histogram statistics based depth matching technique has been used.

FIG. 9 illustrates a CT-generated three-dimensional representation of a 3-ft section of core that was plugged (drilled to extract smaller samples) and slabbed (sliced along the length for geological studies) prior to scanning and for which the selective histogram statistics based depth matching technique has been used.

Figure 10:
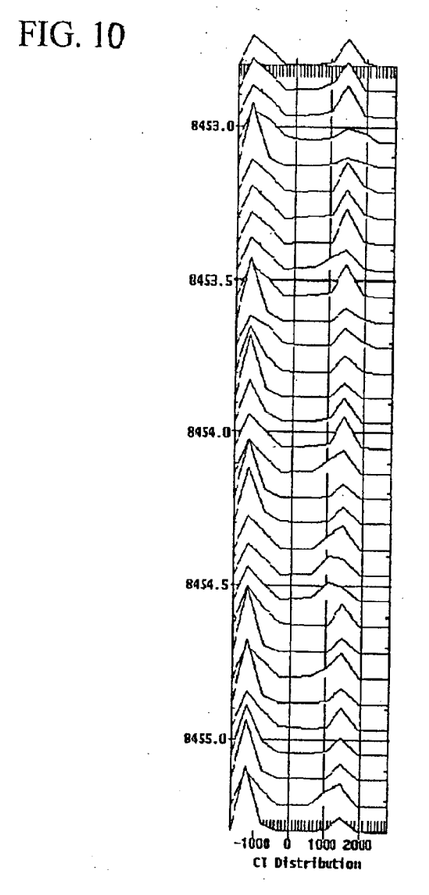
FIG. 10 shows the overall CT number distribution histogram for the core seen in FIG. 9, with two peaks, the one on the left, with low CT numbers (with peak around −1000), representing the non-rock materials, and the second peak on the right, with a range between 1000 and 2500 CT numbers for all the slices, representing the actual rock material.

FIG. 10 shows the overall CT number distribution histogram for the core seen in FIG. 9, with two peaks, the one on the left, with low CT numbers (with peak around −1000), representing the non-rock materials, and the second peak on the right, with a range between 1000 and 2500 CT numbers for all the slices, representing the actual rock material.

Figure 11:
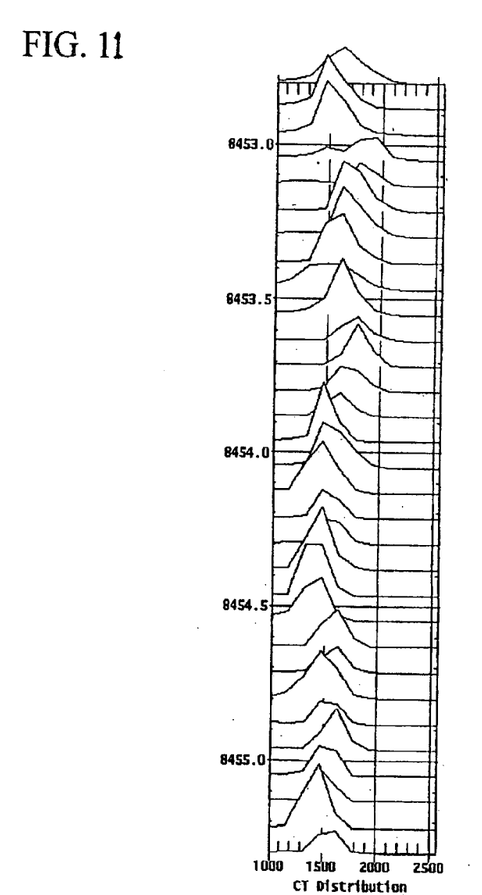
FIG. 11 shows the histogram representing the rock material only, with a range between 1000 and 2500 within which the mean CT number is calculated and used for conversion to bulk densities.

FIG. 11 shows the histogram representing the rock material only, with a range between 1000 and 2500 within which the mean CT number is calculated and used for conversion to bulk densities.

Figure 12:
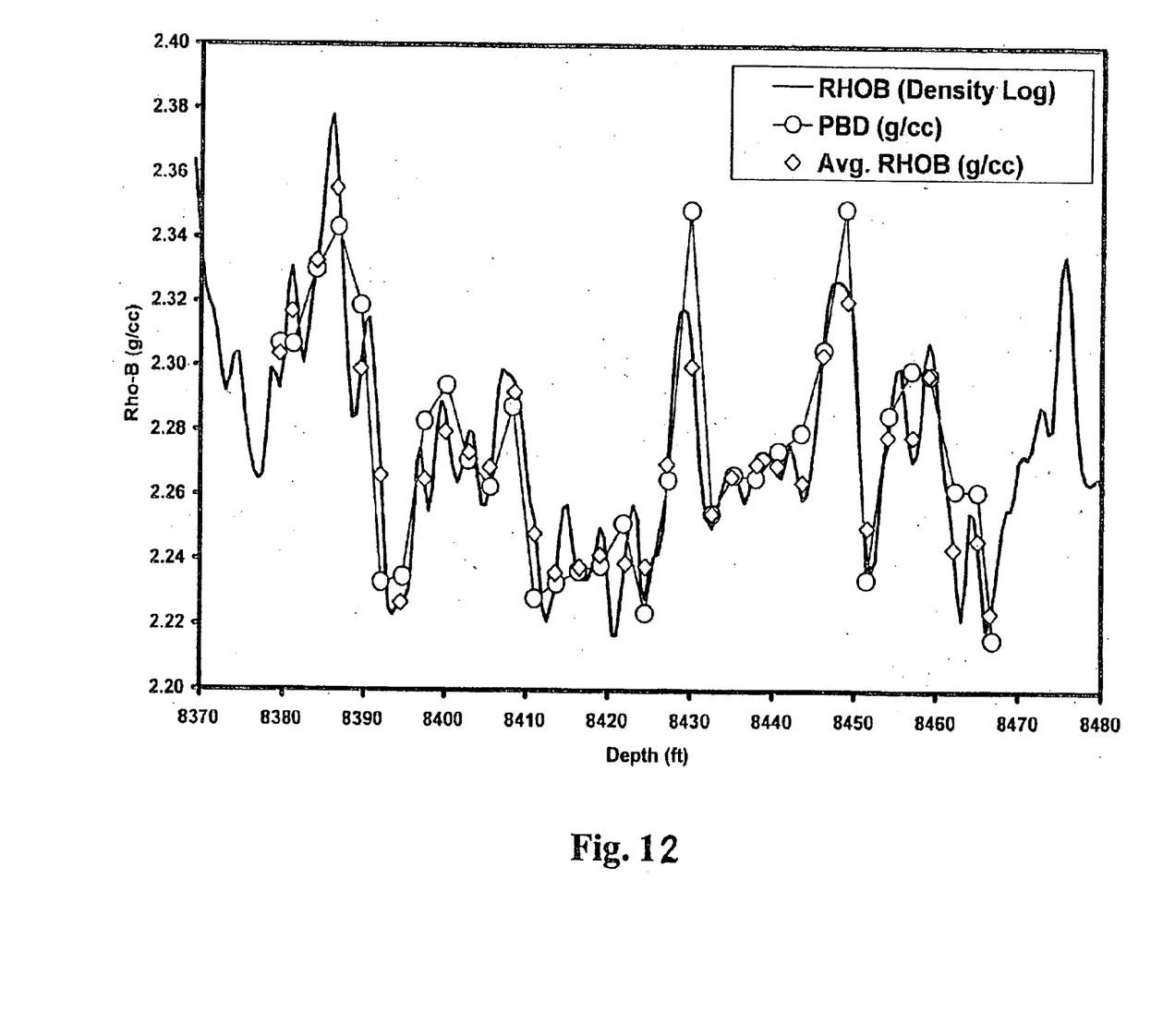
FIG. 12 shows the pseudo-bulk density data generated by the selective histogram statistics technique for 90 feet of core, that were plugged and slabbed, used for depth matching by comparing against the log bulk density data (RHOB, in this case).

FIG. 12 shows the pseudo-bulk density data generated by the selective histogram statistics technique for 90 feet of core, that were plugged and slabbed, used for depth matching by comparing against the log bulk density data (RHOB, in this case).

It has been found that the CT-based depth matching technique in accordance with the present invention performs particularly advantageously in wells drilled in carbonate reservoirs, but this technique may also be applied advantageously in other types of reservoirs, such as sandstone reservoirs. The technique has been successful in finding depth matching for irregularly shaped core samples, samples that have been plugged and slabbed and even for drilled cuttings from carbonate formations. The technique is equally effective in clean sandstone formations.

While the disclosed system and apparatus have been particularly shown and described with respect to the preferred embodiments, it is understood by those skilled in the art that various modifications in form and detail may be made therein without departing from the scope and spirit of the invention. Accordingly, modifications such as those suggested above, but not limited thereto are to be considered within the scope of the invention, which is to be determined by reference to the appended claims.

I claim:

1. A method of depth shifting to correlate information of a core sample taken from a borehole with information derived from an original position of the core sample in the borehole, comprising the steps of:

defining a plurality of scan locations at selected intervals along the core;

scanning the core at each scan location using computed tomography (CT) to generate a respective core slice for each scan location, each core slice including CT data at the respective scan location and each core slice further having a respective first depth assignable thereto based upon a drilling record taken during drilling of the borehole;

generating specified statistics for each core slice, the specified statistics being one of region-of-interest statistics and selective histogram statistics;

converting the CT data for each core slice to first bulk density data in accordance with standardized CT number data and the respective specified statistics;

comparing the first bulk density data to second bulk density data obtained from logging at respective second depths along the borehole; and determining depth shifting appropriate for obtaining a good match between the first and second depths.

2. The method of claim 1, wherein the specified statistics are region-of-interest statistics.

3. The method of claim 1, wherein the specified statistics are selective histogram statistics.

4. The method of claim 1, further comprising the step of obtaining the standardized CT number data by CT scanning of at least one standard object in a same condition as the core.

5. The method of claim 4, wherein each standard object is selected from the group consisting of quartz, Macor, air, water and clean carbonate samples of known densities.

6. The method of claim 1, wherein each core slice includes a 3-D reconstruction of the CT data at the respective scan location.

7. The method of claim 1, wherein said scanning step is performed using high energy X-ray CT.

8. The method of claim 7, wherein said high energy CT is performed substantially at a selected one of 120 kV, 130 kV and 140 kV.

9. The method of claim 1, wherein the specified statistics are circular region-of-interest statistics.

10. The method of claim 1, wherein said converting step includes the steps of:

generating slice bulk density data for each core slice; and calculating at least one average bulk density over the core based upon the slice bulk density data.

11. The method of claim 1, wherein said converting step includes the steps of:

generating statistical CT number data for each core slice based upon the respective CT data and specified statistics;

generating slice bulk density data for each core slice based upon the respective statistical CT number data and the standardized CT number data; and calculating at least one average bulk density over the core based upon the slice bulk density data.

12. The method of claim 11, wherein the specified statistics are region-of-interest statistics.

13. The method of claim 11, wherein the specified statistics are selective histogram statistics.

14. The method of claim 1, wherein said determining step includes the steps of:

plotting the first bulk density data against the first depths and the second bulk density data against the second depths on a same plot; and shifting one of the first bulk density data and the second bulk density data with respect to the other of the first bulk density data and the second bulk density data until a good match between the first and second depths is obtained.

15. The method of claim 14, wherein said shifting step is performed using manual shifting.

* * * * *